United States Patent [19]

Terada et al.

[11] Patent Number: 4,461,912
[45] Date of Patent: Jul. 24, 1984

[54] PHENYLACETIC ACID DERIVATIVES, THEIR PREPARATION AND COMPOSITIONS CONTAINING THEM

[75] Inventors: Atsusuke Terada; Shunji Naruto; Eiichi Misaka, all of Hiromachi, Japan

[73] Assignee: Sankyo Company Limited, Tokyo, Japan

[21] Appl. No.: 447,474

[22] Filed: Dec. 6, 1982

[30] Foreign Application Priority Data

Dec. 18, 1981 [JP] Japan .................. 56/204616

[51] Int. Cl.$^3$ ............ C07C 62/30; C07C 59/00
[52] U.S. Cl. .................. 562/468; 560/57; 560/51; 424/308; 424/317; 562/459; 564/181
[58] Field of Search .............. 560/57; 562/468; 424/308, 317

[56] References Cited

U.S. PATENT DOCUMENTS

| | | | |
|---|---|---|---|
| 3,870,722 | 3/1975 | Houlihan et al. | 562/468 |
| 4,048,065 | 9/1977 | Suen et al. | 560/57 |
| 4,214,095 | 7/1980 | Thiele et al. | 560/57 |
| 4,271,186 | 6/1981 | Förster et al. | 560/57 |
| 4,400,534 | 8/1983 | Terader et al. | 560/57 |

*Primary Examiner*—Paul J. Killos
*Attorney, Agent, or Firm*—Frishauf, Holtz, Goodman & Woodward

[57] ABSTRACT

Phenylacetic derivatives of formula (I):

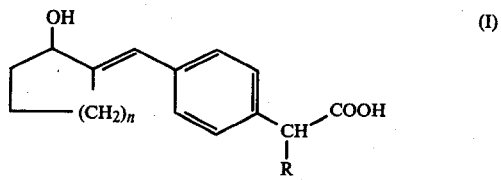

(wherein R represents a hydrogen atom or a $C_1$–$C_3$ alkyl group and n represents an integer from 1 to 3) and salts and esters thereof have analgesic, antipyretic and anti-inflammatory activity and may be prepared by reducing the corresponding acid or ester having an oxo group at the 2-position of the cycloalkylidene ring system and, if necessary, salifying the resulting product.

15 Claims, No Drawings

PHENYLACETIC ACID DERIVATIVES, THEIR PREPARATION AND COMPOSITIONS CONTAINING THEM

BACKGROUND TO THE INVENTION

The present invention relates to a series of new phenylacetic acid derivatives, which have valuable anti-inflammatory, analgesic and antipyretic activities, to a process for preparing these compounds and to pharmaceutical compositions containing them as the active ingredient.

Mild analgesics and antipyretics are amongst the most commonly used of drugs. Most such drugs in common use have side effects which may be distressing or even dangerous to a small percentage of the population—even though the number of people so afflicted may be statistically insignificant, it is better for such persons to employ a different analgesic, antipyretic or anti-inflammatory drug, whose side effects may not be distressing or dangerous to them, rather than continue with the original drug. There is, therefore, a continuing need for new analgesic, antipyretic and anti-inflammatory drugs, to broaden the choice available to the user.

Amongst the known anti-inflammatory drugs are the (2-oxo-cycloalkylidene)methylphenylacetic acid derivatives disclosed in United Kingdom Patent Specification No. 2,002,762, which were demonstrated to have anti-inflammatory and analgesic activities significantly better than similar commercially available drugs.

We have now discovered a series of phenylacetic acid derivatives which have activities comparable with or better than those of the compounds disclosed in United Kingdom Patent Specification No. 2,002,762 and, in particular, which may have an analgesic activity at least three times better than the prior art compounds.

BRIEF SUMMARY OF INVENTION

The compounds of the present invention are those compounds represented by the formula (I):

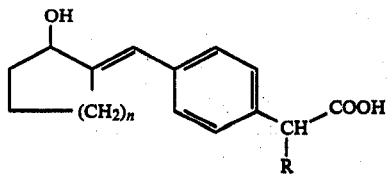
(I)

(wherein R represents a hydrogen atom or a $C_1$–$C_3$ alkyl group and n represents an integer from 1 to 3) and salts and esters thereof.

The compounds of the invention may be prepared by reducing a compound of formula (II):

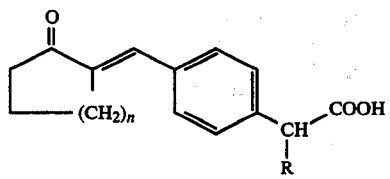
(II)

(wherein R and n are as defined above) or an ester thereof and, if necessary, salifying the resulting product.

The invention also provides a pharmaceutical composition for analgesic, antipyretic or anti-inflammatory use comprising an effective amount of an active ingredient selected from compounds of formula (I), their salts and esters, in admixture with a pharmaceutically acceptable carrier or diluent.

DETAILED DESCRIPTION OF INVENTION

In the compounds of formula (I) and (II), R may represent a hydrogen atom or a $C_1$–$C_3$ alkyl group. Such an alkyl group may be a straight or branched chain group and thus may be a methyl, ethyl, propyl or isopropyl group. Particularly preferred compounds are those in which R represents a hydrogen atom or a methyl group.

n, which represents an integer from 1 to 3, is preferably 1 or 2.

The compounds of the present invention include the esters of compounds of formula (I). Examples of such esters include $C_1$–$C_6$ alkyl esters, aralkyl esters and pyridylmethyl esters. Examples of alkyl esters include the methyl, ethyl, propyl, isopropyl, butyl, isobutyl, pentyl, isopentyl, hexyl and isohexyl esters; of these, $C_1$–$C_4$ alkyl esters are preferred, particularly the ethyl, methyl, propyl, isopropyl and butyl esters. Examples of aralkyl esters include the benzyl and phenethyl esters, in which the aromatic ring may be substituted or unsubstituted. Where it is substituted, the substituents may be one or more of the following: lower alkyl groups, e.g. methyl, ethyl, propyl or isopropyl groups; lower alkoxy groups, e.g. methoxy, ethoxy, propoxy or isopropoxy groups; halogen atoms, e.g. fluorine, chlorine or bromine atoms; or trifluoromethyl groups. In the case of pyridylmethyl esters, these may be the 2-, 3- or 4-pyridylmethyl esters.

Particularly preferred compounds are the free carboxylic acid of formula (I) or the $C_1$–$C_4$ alkyl esters, particularly the free carboxylic acid.

The compounds of the invention may also exist in the form of salts. The nature of the salts is not critical to the invention, although, where the salts themselves are intended for therapeutic use, they should, of course, be pharmaceutically acceptable salts. Examples of such salts include the alkali and alkaline earth metal salts (such as the sodium or calcium salt), the aluminium salt, the ammonium salt, salts with organic bases (such as triethylamine, dicyclohexylamine, dibenzylamine, morpholine, pyridine or N-ethylpiperidine) and salts with basic amino acids (such as glycine or arginine). The salts may be prepared from the free carboxylic acid of formula (I) by a conventional salification process.

The compounds of the invention have an asymmetric carbon atom, and thus they can exist as optical isomers. The present invention embraces not only the individual optical isomers of the compounds of the invention, but also racemic and other mixtures thereof. Accordingly, where the compound of the invention is obtained in the form of a mixture of optical isomers, this mixture may be employed as it is, or the individual isomers may be obtained using resolution techniques such as are well known in the art.

Specific examples of compounds of the invention are listed below:

2-[4-(2-Hydroxycyclohexylidenemethyl)phenyl]propionic acid
Methyl 2-[4-(2-hydroxycyclohexylidenemethyl)phenyl]propionate
Ethyl 2-[4-(2-hydroxycyclohexylidenemethyl)phenyl]propionate Butyl 2-[4-(2-hydroxycyclohexylidenemethyl)phenyl]propionate
Sodium 2-[4-(2-hydroxycyclohexylidenemethyl)phenyl]propionate
Arginine 2-[4-(2-hydroxycyclohexylidenemethyl)phenyl]propionate
Lysine 2-[4-(2-hydroxycyclohexylidenemethyl)phenyl]propionate
4-(2-Hydroxycyclohexylidenemethyl)phenylacetic acid
2-[4-(2-Hydroxycyclopentylidenemethyl)phenyl]propionic acid
Methyl 2-[4-(2-hydroxycyclopentylidenemethyl)phenyl]propionate
Ethyl 2-[4-(2-hydroxycyclopentylidenemethyl)phenyl]propionate
Propyl 2-[4-(2-hydroxycyclopentylidenemethyl)phenyl]propionate
Sodium 2-[4-(2-hydroxycyclopentylidenemethyl)phenyl]propionate
Arginine 2-[4-(2-hydroxycyclopentylidenemethyl)phenyl]propionate
Lysine 2-[4-(2-hydroxycyclopentylidenemethyl)phenyl]propionate
4-(2-Hydroxycyclopentylidenemethyl)phenylacetic acid
2-[4-(2-Hydroxycycloheptylidenemethyl)phenyl]propionic acid
4-(2-Hydroxycycloheptylidenemethyl)phenylacetic acid.

The compounds of formula (I) and their esters may be prepared by reducing a compound of formula (II) or an ester thereof. Conventional reducing agents may be employed in this process and the nature of the reducing agent is not critical, provided that it does not affect other parts of the molecule. Preferred reducing agents are the alkali metal borohydrides, such as sodium borohydride or sodium cyanoborohydride. The reaction will normally be carried out in the presence of a solvent, the nature of which is not critical, provided it has no adverse effect upon the reaction. Suitable organic solvents which may be employed include: ethers, such as diethyl ether or tetrahydrofuran; aromatic hydrocarbons, such as benzene or toluene; and alcohols, such as methanol or ethanol. There is no particular limitation on the reaction temperature, although we generally prefer to carry out the reaction at a temperature which may range from ice-cool to the boiling temperature of the solvent employed. The time required for the reaction will vary, depending mainly upon the reaction temperature and the nature of the reducing agent employed, although a period of from 10 minutes to 3 hours will usually suffice. After completion of the reaction, the compound of formula (I) or its ester may be recovered from the reaction mixture by conventional means.

Where the desired end product is a salt of the compound of formula (I), this may be prepared by conventional salification of the free acid, which may be effected prior to, after or in the course of the recovery process.

The compounds of the invention have been tested for pharmacological activity and found to exhibit anti-inflammatory, analgesic and antipyretic activities. Details of the pharmacological tests are as follows:

Carrageenin oedema test for anti-inflammatory activity

Male Wistar rats weighing 120–150 g were fasted overnight and then received a test compound per os as an aqueous tragacanth suspension. 30 minutes later, inflammation was induced by the subcutaneous injection of 0.05 ml of a 1% carrageenin suspension into the plantar tissue of a hind paw of each rat [Winter et al., Proc. Soc. Exp. Biol. Med., 111, 544 (1962)]. The antioedema activity was measured volumetrically, by assessing the response, as calculated from the following equation:

$$\text{Response} = (V - V_o)/V_o$$

where $V_o$ and $V$ represent, respectively, the paw volume immediately before and 3 hours after the carrageenin injection. The test compounds were administered at various doses and the results are reported in the following Table as the $ID_{50}$, that is the inhibitory dose required to inhibit the response by 50%.

Pain test for analgesic activity

This test was conducted according to a modification of the method reported by L. O. Randall and J. J. Selitto in Arch. Int. Pharmacodyn., 11, 409 (1959), proposed by Winter and Flatake (1957).

Male Wistar-Imamichi rats of 4 weeks of age and weighing 60–90 g were injected with 0.1 ml of a 20% by weight suspension of Brewers' yeast in the right hind paw. 4 hours later, rats which had a pain threshold to pressure-induced pain less than 10×30 g were selected. Each of these was given orally a test compound as an aqueous tragacanth suspension. 1 and 2 hours after administration of the test compound, the pain threshold was determined by observing pain responses (such as struggling or squeaking) when the inflamed or normal paw was subjected to pressure by a machine (Ugo-Basile). An "effective" animal was defined, in accordance with Blane's method (1968), as an animal which showed at least twice the mean pain threshold of control animals. The $ED_{50}$ was calculated by the method of Litchfield and Wilcoxon (1949).

The results are reported in the following Table, in which the compounds used are identified by the following codes:

A: 2-[4-(2-hydroxycyclohexylidenemethyl)phenyl]propionic acid;
B: Indomethacin;
C: 2-[4-(2-oxocyclohexylidenemethyl)phenyl]propionic acid (disclosed in United Kingdom Patent Specification No. 2,002,762).

TABLE

| Compound | Anti-inflammatory activity $ID_{50}$ | Analgesic activity $ED_{50}$ |
|---|---|---|
| A | 0.98 | 0.35 |
| B | 2.2 | 1.6 |
| C | 1.2 | 0.94 |

The results shown above demonstrate that the compound of the invention is more effective both than the commercially available indomethacin and than the closest prior art compound, i.e. the compound from which it is prepared by reduction.

The compounds of the invention are preferably administered in admixture with a carrier or diluent in the form of a conventional pharmaceutical composition, preferably orally or rectally. Compositions for oral administration may be formulated as, for example, tablets, capsules, granules, powders or syrups, whilst compositions for rectal administration may be in the form of suppositories. The compounds are also effective when applied topically, for example in the form of an ointment or a cream. The dosage employed will vary depending upon the condition, age and body weight of the patient, but usually the dose for oral administration would be from 30 to 200 mg per day for an adult, which may be administered in a single dose or in divided doses.

The preparation of the compounds of the invention is further illustrated by the following Examples.

EXAMPLE 1

2-[4-(2-Hydroxycyclohexylidenemethyl)phenyl]propionic acid 2 g of 2-[4-(2-oxocyclohexylidenemethyl)phenyl]propionic acid (which may be prepared as described in United Kingdom Patent Specification No. 2,002,762) and 0.6 g of sodium cyanoborohydride were dissolved in 40 ml of methanol. The pH of the solution was adjusted to a value of 3 by the addition of 6N hydrochloric acid, whilst ice-cooling. The mixture was then heated under reflux for 1 hour, after which a saturated aqueous solution of sodium chloride was added and the mixture was extracted with diethyl ether. The extract was dried and the solvent was then distilled off. The residue was purified by high speed liquid chromatography, to give the desired compound in a crude form. This was recrystallised from a 1:1 by volume mixture of ethyl acetate and hexane, to give 350 mg of the title compound, melting at 135°–136° C.

Elemental analysis: Calculated for $C_{16}H_{20}O_3$: C, 73.82%; H, 7.74%. Found: C, 73.66%; H, 7.65%.

EXAMPLE 2

2-[4-(2-Hydroxycyclopentylidenemethyl)phenyl]propionic acid 123 mg of 2-[4-(2-oxocyclopentylidenemethyl)phenyl]propionic acid (which can be prepared as described in United Kingdom Patent Specification No. 2,002,762) and 75 mg of sodium cyanoborohydride were dissolved in 5 ml of methanol. The pH of the solution was adjusted to a value of 3 by the addition of 6N hydrochloric acid, whilst ice-cooling. The mixture was stirred under reflux for 40 minutes, after which it was diluted with ice-water and then extracted with diethyl ether. The extract was washed with water and then the solvent was distilled off to give crystals. These were recrystallised from a 1:1 by volume mixture of ethyl acetate and hexane, to give 80 mg of the title compound, melting at 125°–132° C.

Elemental analysis: Calculated for: $C_{15}H_{18}O_3$: C, 73.14%; H, 7.37%. Found: C, 73.01%, H, 7.40%.

We claim:

1. Compounds of formula (I):

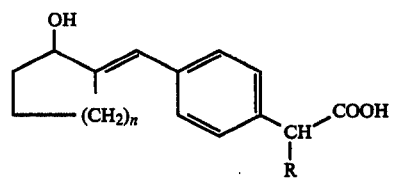

(wherein R represents a hydrogen atom or a $C_1$–$C_3$ alkyl group and n represents an integer from 1 to 3) and pharmaceutically acceptable salts and esters thereof.

2. Compounds as claimed in claim 1, wherein R represents a hydrogen atom.

3. Compounds as claimed in claim 1, wherein R represents a methyl group.

4. Compounds as claimed in claim 1, wherein n is 1 or 2.

5. Compounds as claimed in claim 1, which are the esters of said compounds of formula (I), wherein the ester moiety is selected from the group consisting of $C_1$–$C_6$ alkyl groups; aralkyl groups; substituted aralkyl groups having at least one substituent selected from the group consisting of lower alkyl, lower alkoxy, halogen, and trifluoromethyl; and pyridylmethyl groups.

6. Compounds as claimed in claim 1, which are the $C_1$–$C_4$ alkyl esters of said compounds of formula (I).

7. Compounds as claimed in claim 1, which are the alkali metal, alkaline earth metal, aluminium, ammonium, organic base or amino acid salts of said compounds of formula (I).

8. A process for preparing a compound of formula (I):

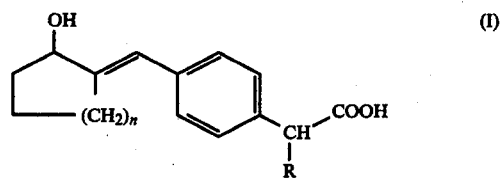

(wherein R represents a hydrogen atom or a $C_1$–$C_3$ alkyl group and n represents an integer from 1 to 3) and esters and salts of said compound of formula (I), which comprises reducing a compound of formula (II):

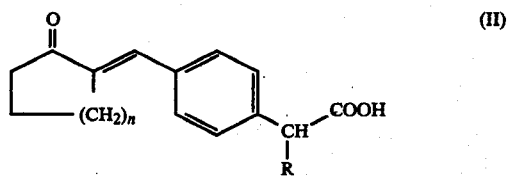

(wherein R and n are as defined above) or an ester thereof and, if necessary, salifying the resulting product.

9. A process as claimed in claim 8, wherein the reduction is effected with an alkali metal borohydride as reducing agent.

10. A process as claimed in claim 9, wherein said alkali metal borohydride is selected from the group consisting of sodium borohydride and sodium cyanoborohydride.

11. A process as claimed in claim 8, wherein R represents a hydrogen atom or a methyl group and n is 1 or 2 and there is employed said compound of formula (II) or a $C_1$–$C_4$ alkyl ester thereof.

12. A pharmaceutical composition for analgesic, antipyretic or anti-inflammatory use, comprising an effective amount of an active ingredient selected from compounds of formula (I):

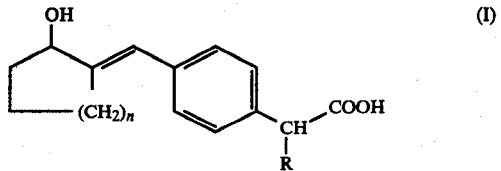

(wherein R represents a hydrogen atom or a $C_1-C_3$ alkyl group and n represents an integer from 1 to 3), their pharmaceutically acceptable salts and esters, in admixture with a pharmaceutically acceptable carrier or diluent.

13. A composition as claimed in claim 12, formulated for oral, rectal or topical application.

14. A composition as claimed in claim 12, wherein said active ingredient is selected from the group consisting of 2-[4-(2-hydroxycyclohexylidenemethyl)phenyl]propionic acid and 2-[4-(2-hydroxycyclopentylidenemethyl)phenyl]propionic acid.

15. Compounds as claimed in claim 1, selected from the group consisting of 2-[4-(2-hydroxycyclohexylidenemethyl)phenyl]propionic acid and 2-[4-(2-hydroxycyclopentylidenemethyl)phenyl]propionic acid.

* * * * *